(12) United States Patent
Groβ et al.

(10) Patent No.: US 7,905,658 B2
(45) Date of Patent: Mar. 15, 2011

(54) C-ARM MOUNTED ON A ROBOTIC ARM

(75) Inventors: Stefan Groβ, Trabitz (DE); Dieter Heinl, Erbendorf (DE)

(73) Assignee: Siemens Aktiengesellschaft, München (DE)

( * ) Notice: Subject to any disclaimer, the term of this patent is extended or adjusted under 35 U.S.C. 154(b) by 90 days.

(21) Appl. No.: 12/348,479

(22) Filed: Jan. 5, 2009

(65) Prior Publication Data

US 2009/0185662 A1     Jul. 23, 2009

(30) Foreign Application Priority Data

Jan. 10, 2008    (DE) .................... 10 2008 003 815

(51) Int. Cl.
    *H05G 1/02*    (2006.01)
(52) U.S. Cl. .................... 378/193; 378/197; 378/198
(58) Field of Classification Search .................. 378/193, 378/197, 198
    See application file for complete search history.

(56) References Cited

U.S. PATENT DOCUMENTS

| 5,048,069 | A  | * | 9/1991 | Siczek ........................ 378/197 |
| 7,108,421 | B2 | * | 9/2006 | Gregerson et al. ............ 378/197 |
| 7,500,784 | B2 | * | 3/2009 | Grebner et al. ............... 378/198 |
| 2009/0180592 | A1 | * | 7/2009 | Gross et al. ................... 378/189 |

FOREIGN PATENT DOCUMENTS

DE    10 2005 012 700 A1    9/2006
DE       102008003088 A1    7/2009

OTHER PUBLICATIONS

German Office Action dated Jan. 20, 2010 with English translation.
German Office Action dated Nov. 5, 2008 with English translation.

* cited by examiner

*Primary Examiner* — Jurie Yun
(74) *Attorney, Agent, or Firm* — Brinks Hofer Gilson & Lione

(57) ABSTRACT

An X-ray apparatus is provided. The X-ray apparatus includes a C-arm mounted on a robotic arm that is operable to be rotated about an axis of rotation. A radiation source and a radiation detector are arranged on the C-arm. The distance between the radiation source and radiation detector may be varied by a lifting device. The radiation source may be moved longitudinally relative to the radiation detector, or vice versa. The C-arm may include two arm sections that can be moved relative to one another by a lifting device. The radiation source is arranged on the one arm section and the radiation receiver is arranged on the other arm section.

15 Claims, 2 Drawing Sheets

C-ARM MOUNTED ON A ROBOTIC ARM

This patent document claims the benefit of DE 10 2008 003 815.6, filed Jan. 10, 2008, which is hereby incorporated by reference.

BACKGROUND

The present embodiments relate to an X-ray apparatus comprising a C-arm mounted on a robotic arm.

X-ray apparatuses have a C-arm arranged on a stand, which stands on the floor. The C-arm allows rotation by way of a rotation guide about an axis which is generally oriented horizontally. In the rotation guide, the C-arm can be rotated around an isocenter along an arc-shaped guideway. When the C-arm is moved at a considerable speed along the rotation guide, a lightweight C-arm may be used to achieve the best possible dynamics. An angiographic X-ray apparatus can be cited as an example here. For this reason, C-arms made from extruded sections are normally used which have an essentially rectangular hollow profile in terms of their cross-section.

Instead of a floor stand and connecting the C-arm by the rotation guide, which elements serve to implement the required levels of freedom of movement for the C-arm motion and positioning, a C-arm may be mounted on an industrial robot with a robotic arm and a corresponding control facility. The required levels of freedom are guaranteed by the six axes of movement of the robot. The C-arm may be mounted and may be capable of rotation directly on the robotic arm.

The distance between the radiation source and the radiation detector, which may be the film-focus distance, can be varied by a lifting device. The radiation receiver may be moved in linear fashion along the central beam. As a result, the lifting device is situated directly adjacent to the radiation receiver at the end of the C-arm. This is disadvantageous insofar as the C-arm overhangs a long way as a result because the lifting device, which enables the desired lift, extends a relatively long way outwards when viewed radially. This sometimes restricts the movability of the C-arm since some positions cannot be reached on account of a possible collision of the overhanging lifting device. The center of gravity of the C-arm that results from the arrangement employed there is also not necessarily ideal.

SUMMARY & DESCRIPTION

The present embodiments may obviate one or more of the drawbacks or limitations inherent in the related art. For example, in one embodiment, an X-ray apparatus includes a C-arm, which in spite of the arrangement of a lifting device is constructed so as to overhang less far.

In one embodiment, an X-ray apparatus includes a C-arm. The C-arm is mounted on a robotic arm. The C-arm is capable of rotation about an axis of rotation. A radiation source and a radiation detector are disposed on the C-arm. The distance between the radiation source and radiation detector can be varied by a lifting device, by which the radiation receiver can be moved longitudinally relative to the radiation source, or vice versa.

The C-arm may include two arm sections which can be moved relative to one another by the lifting device, whereby the radiation source is arranged on the one arm section and the radiation receiver on the other arm section.

A two-part implementation of the C-arm is provided. The two arm sections of a hollow arm, which may be accessible from the side, can be moved relative to one another by the lifting device arranged in the interior of the arm. The arm enables the lifting device to be arranged in the area of the interface of the two arm sections, for example, in the area adjacent to the pivot bearing of the C-arm on the robotic arm. The center of gravity can be optimized and is then located as close as possible to the axis of rotation. Accordingly, the motion dynamics may be enhanced. The weight on the end of the arm carrying the radiation receiver is consequently no longer dictated to a considerable extent by the lifting device but merely by the radiation receiver situated there because the lifting device is arranged on the pivoting connection of the arm, for example, on the robotic arm. The lifting device may be arranged on the pivoting connection because it includes hollow arm sections and is integrated in the interior of the arm. The C-arm in the area of the radiation detector is also no longer overhanging to the side, rather its form is determined essentially by the geometry of the arm.

The C-arm may be pivotably mounted by way of one arm section, while the other arm section is guided on or in the latter. No additional complex mounting or fixing mechanisms are therefore employed. Rather the one C-arm section, which has a fixed position with reference to the lifting movement and relative to which the other C-arm is moved by the lifting device, is used directly for the fixing to the robotic arm. Corresponding fixing facilities are provided, or arranged, on this arm section. The other arm section is guided to be movable in linear fashion on or in this first arm section, that is to say it can be moved in linear fashion by the lifting device, such that a linear movement of the radiation source relative to the radiation detector results. Guide rails may be provided for the linear guidance. The guide rails may be disposed on the arm section whose position is fixed, on which guide rails run corresponding guide sections of the other arm section in each case.

The lifting device may include a drive motor and a lifting mechanism which can be actuated by the motor. A step-up or reduction gear unit may be connected downstream of the drive motor, depending on how the drive motor or the lifting mechanism is designed.

The lifting mechanism may include a stationary cog wheel, which can be driven by the drive motor or the gear unit connected downstream and a toothed rack arranged on the arm section to be moved, with which the cog wheel meshes. Alternatively, the lifting mechanism may have a stationary threaded spindle, which can be driven by the drive motor, on which runs at least one threaded nut connected to the arm section to be moved. The listing of different mechanical designs is not exclusive. Any mechanical embodiment may be used, which has a small construction in order to allow integration into the arm and which allows an adequate lift.

Alternatively, a lifting device may include a positioning cylinder that may be actuated electrically, hydraulically, or pneumatically. The positioning cylinder may be coupled to both arm sections. The positioning cylinder may be used as a mechanical lifting device.

The hollow C-arm used can be configured to be open from at least one access side. The arm configuration, which is open at least in sections on one or multiple sides, allows the overall weight of the C-arm to be reduced. The geometry of the C-arm is naturally designed in accordance with the required strength and vibration criteria. However, in spite of the open construction, the required strength and vibration criteria can be adhered to or attained. The open structure also offers the advantage that the possibility exists in principle when using the C-arm in conjunction with an industrial robot or a robotic arm to enable at least one part or approximately all the electronics components which are used for operation of the radiation source and of the of the radiation receiver to be integrated in the interior of the C-arm. In one embodiment, the electronics components, which are normally assemblies or cables having relatively small dimensions, can be installed in the interior of the arm. Therefore they no longer need to be arranged separately and connected by way of corresponding cable or control line connections to the arm-side operating components but are moved together with the C-arm. Since the assemblies are relatively light in weight on account of the high integration density of the electronics components. In other words, the weight of all the electronics components to be integrated is not excessively great, only a relatively slight increase in weight of the C-arm results, such that the requirements for high dynamic performance can still be met in spite of the integration of the electronics components.

The C-arm with the open structure offers an advantageous field of application both in the case of previously common X-ray apparatuses having a floor stand, in which X-ray apparatus the electronics components are then not integrated in the C-arm but this is lighter in weight compared with previous systems, and also a field of application in the case of robotic X-ray units in which at least a part of or all the electronics components are then integrated in the interior of the arm.

The C-arm may be hollow and accessible to the side essentially over its entire length, such that adequate accessible receiving space is available in which the electronics components can be arranged.

For ease of installation and accessibility the interior of the C-arm is expediently accessible from access sides situated opposite one another. The two side surfaces in the case of a rectangular arm profile seen in cross-section. This makes it possible for installation or maintenance purposes to reach the positions in question from both sides, which makes for simpler working conditions.

The C-arm may be in the form of a framework on one access side, that is to say struts are provided there arranged in the form of a framework, whereby this applies to both sides in the case of an arm structure, which is open on both sides. The framework construction may be realized on both sides, for example, in the same implementation. The corresponding structure can be manufactured because the C-arm may be implemented as a casting. The physical form of the framework structure and accordingly the arrangement of the struts may be selected with respect of the weight optimization, in order to save the greatest possible quantity of material. The strut arrangement may be designed so as to attain the desired mechanical properties. Material can be saved principally in the area of low mechanical stresses or loadings, whereas in areas of greater mechanical loading corresponding struts are provided in an appropriate angular arrangement with respect to one another or to the other arm sections. The design of the structure conforms to the given geometric and mechanical guidelines.

Alternatively, in order to use a framework-type structure on one or two sides lying opposite one another, the C-arm may be subdivided in a cartridge form in the interior by dividing walls. Such a structure may be realized with a casting. The cartridge form, which is accessible from one side for example, likewise enables the integration of a multiplicity of required electronics components. The intermediate (dividing) walls may be opened at least in sections in order to route connecting or supply lines through the intermediate walls. The access side may be completely open because the stability is realized by the constructed dividing walls in conjunction with the other three closed side walls.

All or some of the access sides may be closed by a detachable cladding that can, however, be removed simply and quickly for installation or maintenance purposes.

DETAILED DESCRIPTION

Figure 1:
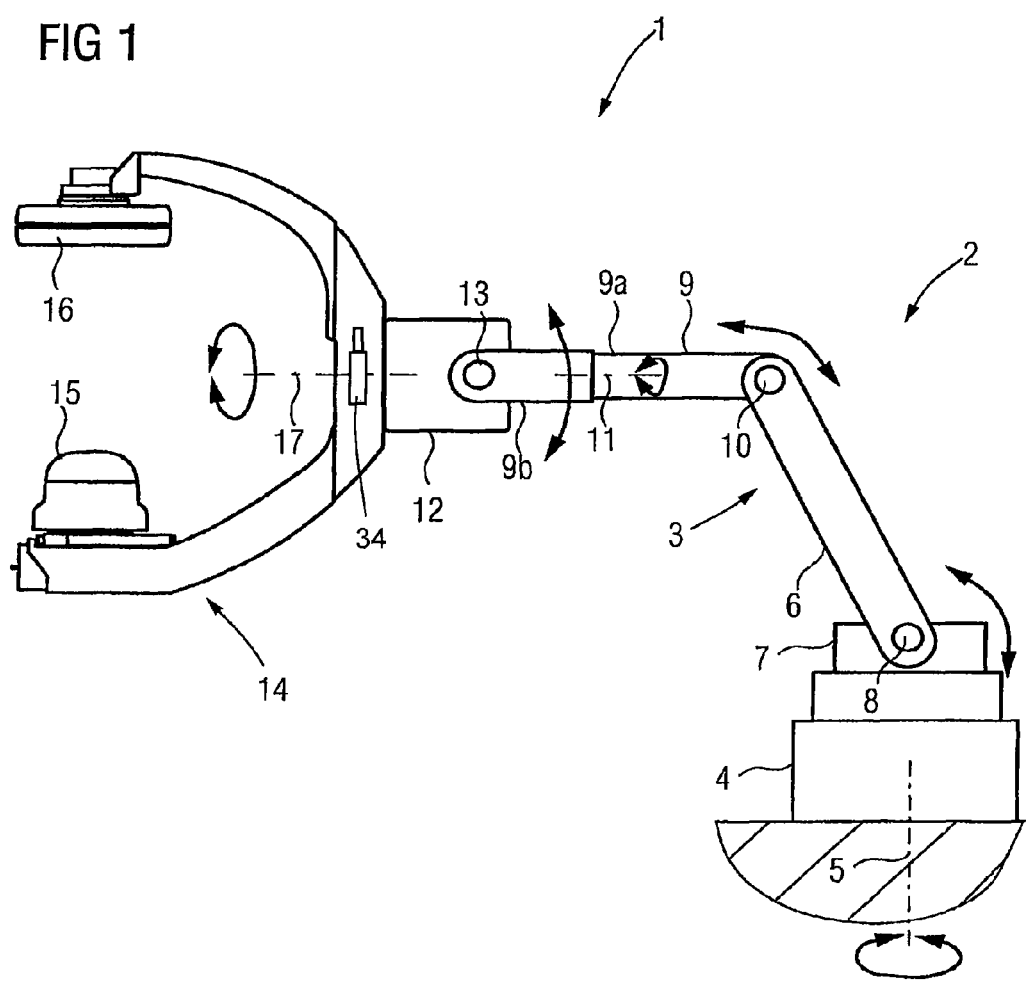
FIG. 1 shows one embodiment of an X-ray apparatus including a C-arm that is arranged on an industrial robot.

FIG. 1 shows an X-ray apparatus 1. The X-ray apparatus 1 includes an industrial robot 2, having a robotic arm 3, which is accommodated on a base 4 that is arranged on the floor. The robotic arm 3 can rotate as a whole on the base around a vertical axis 5. It is accommodated on the base 4 by a first robotic arm 6 on a base part 7 capable of rotation about the vertical axis, on which it can additionally be pivoted about a horizontal axis 8. On the first robotic arm 6 is situated a second robotic arm 9 which can be pivoted on it about a second horizontal axis 10. The second robotic arm 9 consists of the first arm section 9a, which is arranged on the first robotic arm 6, and also a second arm section 9b which for its part is rotatable about a further axis 11 relative to the arm section 9a. On the arm section 9b is additionally situated a C-arm holder 12, which can rotate around the axis 13. The C-arm 14, on which are arranged a radiation source 15 and also a radiation receiver 16, is for its part capable of rotation on the C-arm holder 12 about a further axis of rotation 17. A 6-axis system is provided. The 6-axis system allows free movement of the C-arm 14 in space.

Figure 2:
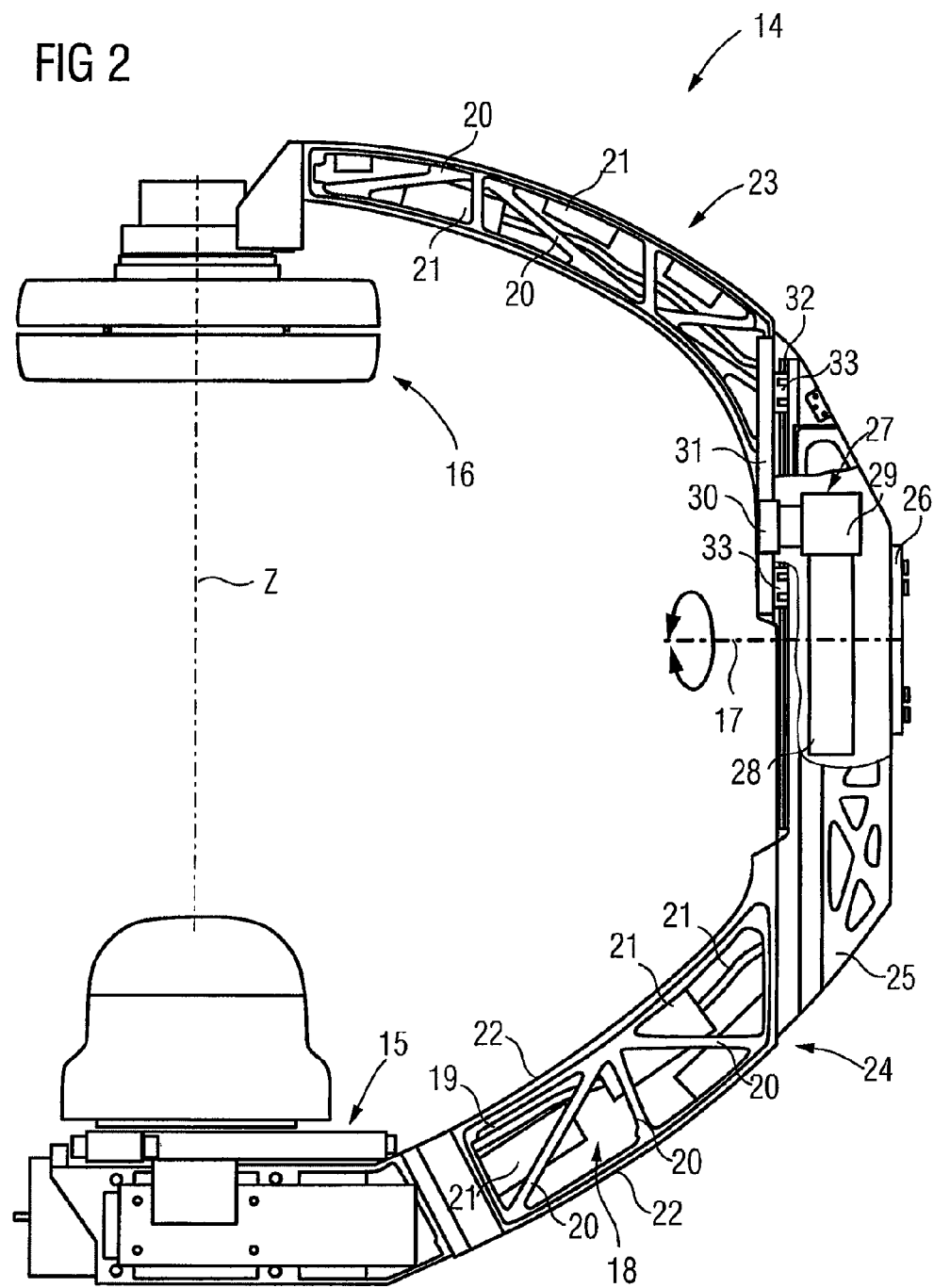
FIG. 2 shows one embodiment of the C-arm in section.

The C-arm 14 is illustrated in detail in FIG. 2. The C-arm 14 has an open structure and is hollow in the interior. Two opposite sides (in the side view shown in FIG. 2 only the one side can naturally be seen) are open, that is to say corresponding access sides 18 are realized which give access to the arm interior 19. The two access sides lying opposite one another have a framework-type structure, or struts arranged in the form of a framework, whose dimensions and arrangement are chosen such that the best possible rigidity can be realized with the minimum usage of material. These two access sides 18, which may be closed by appropriate cladding parts, then make it possible to enable the integration of electronics components 21, of which various ones are represented here by way of example, in the interior of the C-arm 14. These electronics components 21 are used for the operation of the radiation source 15 and the radiation detector 16. With regard to these electronics components, they can be any desired components or also cables. They are secured to the struts 20 or to the remaining side walls 22 of the C-arm by suitable fasteners.

The C-arm 14 includes two arm sections 23, 24, which may be implemented as cast metal parts, enabling the framework structure to be formed in a simple manner. The arm section 24 has a mounting section 25, by which it can be arranged on the C-arm holder 12 of the robotic arm 3 with a suitable mounting flange 26. This mounting section 25 can be an integral element of the arm section 24, but it can also be connected as a separate casting to the second arm section having the open access side 18 in order to then form the first arm section 24 as a whole.

The arm section 23 may be moved in linear fashion by a lifting device 27 relative to the arm section 24 that is arranged in a fixed position on the C-arm holder 12. The lifting device 27 may be integrated in the interior of the C-arm. Accordingly, the distance of the radiation detector 16 may be varied relative to the radiation source 15 by shifting the radiation detector 16 along the central beam Z. The lifting device 27 comprises a drive motor 28, downstream of which is connected a gear unit 29 which serves to drive a cog wheel 30. This lifting mechanism, which includes the drive motor 28, the gear unit 29 and the cog wheel 30, is arranged in a fixed position on the arm section 24. The cog wheel 30 meshes with a toothed rack 31 which is arranged on the arm section 23. On the arm section 24 or on its mounting section 25 are formed guide rails 32 situated opposite one another, on which run corresponding runner elements 33 of the movable arm section 23. An exact linear guidance of the arm sections 23 and 24 with respect to one another is realized.

Depending on how the drive motor 28 is controlled by way of the control facility, which controls the entire operation of the X-ray apparatus 1 and which is not described in detail here but is of course present, the motion of the cog wheel 30 can be varied in respect of both the direction of rotation and also the speed of rotation, by which the speed of motion and direction of motion of the arm section 23 carrying the radiation receiver 16 can be varied. A suitable position sensing system may determine (sense) the exact positioning of the arm section 23 and thus of the radiation receiver 16 relative to the radiation source 15, whereby the control of the lifting device 27 can be effected depending on such a sensing of position.

Even though a rack and pinion drive is described, the integration of a spindle drive may be used. A drive spindle on which are threaded one or more suitable spindle nuts, which would be connected with the arm section 23, would then be turned by the drive motor. Alternatively, a lifting device may include a positioning cylinder 34 that may be actuated electrically, hydraulically, or pneumatically. The positioning cylinder 34 may be coupled to both arm sections. The positioning cylinder may 34 be used as a mechanical lifting device. The arm section 23 may be guided in linear fashion by linear guides (e.g., guide rails 32, runner elements 33). Alternatively, in place of a framework-like strut structure, the arm interior may be subdivided using dividing walls in a cartridge form. For example, the dividing walls may form slide-in bays that are open from the side. The electronics components 21 can then be integrated into these cartridge-like slide-in bays. In order to enable communication or supply lines to be taken through the arm interior, these dividing walls are broken through locally. A corresponding side cladding would naturally also be employed here.

The C-arm provides the opportunity to make considerable weight savings, resulting from the open arm structure. The integration of the lifting device into the arm interior in the immediate area of the axis of rotation 17, around which the C-arm 14 can rotate relative to the arm holder 12, continues to be advantageous in respect of the optimization of the center of gravity of the arm. The lifting device 27 is situated in the immediate vicinity of where the C-arm is mounted on the robotic arm, the linear movement axis, along which the arm section 23 and the radiation receiver 16 can move relative to the arm section 24, or the radiation source 15, is perpendicular to the axis of rotation 17 in this arrangement. A further advantage of integrating the lifting device 27 into the arm interior in the area of the pivoting connection with the robotic arm also consists in the fact that the C-arm is no longer constructed as high on the detector side as in the case of known X-ray apparatuses. This is because the lifting device arranged at the end of the arm in the case of known X-ray apparatuses normally required a considerable construction space, that is to say it extended away from the exterior of the arm, viewed radially. This was sometimes a limiting factor for an arm movement. Some arm positions could not be reached as a result of the overhanging arm.

The invention claimed is:

1. An X-ray apparatus comprising:
   a robotic arm;
   a radiation source;
   a radiation detector; and
   a C-arm mounted on the robotic arm, the C-arm being operable to rotate about an axis of rotation, the radiation source and the radiation detector being disposed on the C-arm, such that the distance between the radiation source and the radiation detector is varied by a lifting device, the radiation source being operable to be moved longitudinally relative to the radiation detector,
   wherein the C-arm includes a first arm section and a second arm section, which are moved relative to one another by the lifting device, the radiation source being arranged on the first arm section and the radiation detector being arranged on the second arm section, and
   wherein the C-arm is pivotably mounted by one of the first and second arm sections, while the other of the first and second arm sections is the only arm section that is guided on or in the mounted arm section.

2. The X-ray apparatus as claimed in claim 1, wherein the lifting device is arranged adjacent to a pivot bearing of the C-arm.

3. The X-ray apparatus as claimed in claim 1, further comprising guide rails that are operable to guide the first and second arm sections.

4. The X-ray apparatus as claimed in claim 1, wherein the lifting device is arranged in the interior of the first arm section, the second arm section, or a combination of both the first and second arm sections, the first arm section and second arm section being hollow at least in sections.

5. The X-ray apparatus as claimed in claim 1, wherein the lifting device includes a drive motor and a lifting mechanism that can be is operable to be actuated by the drive motor.

6. The X-ray apparatus as claimed in claim 5, wherein the lifting mechanism includes a stationary cog wheel that is operable to be driven by the drive motor and a toothed rack arranged on the second arm section to be moved, with which the cog wheel meshes.

7. The X-ray apparatus as claimed in claim 5, wherein the lifting mechanism includes a stationary threaded spindle that can is operable to be driven by the drive motor, a threaded nut connected to the second arm section to be moved running on the stationary threaded spindle.

8. The X-ray apparatus as claimed in claim 1, wherein the lifting device has a positioning cylinder that is operable to be actuated electrically, hydraulically or pneumatically.

9. The X-ray apparatus as claimed in claim 8, wherein the lifting device is coupled to the first and second arm sections.

10. The X-ray apparatus as claimed in claim 9, further comprising guide rails that are operable to guide the first and second arm sections.

11. The X-ray apparatus as claimed in claim 1, wherein the first and second arm sections are hollow bodies.

12. The X-ray apparatus as claimed in claim 11, wherein the first and second arm sections further comprises a framework structure comprising stiffening struts on one or more open sides.

13. An X-ray apparatus comprising:
    a robotic arm;
    a radiation source;
    a radiation detector; and
    a C-arm mounted on the robotic arm, the C-arm being operable to rotate about an axis of rotation, the radiation source and the radiation detector being disposed on the C-arm, such that the distance between the radiation source and the radiation detector is varied by a lifting device, the radiation detector being operable to be moved longitudinally relative to the radiation source, wherein the C-arm includes only a first arm section and a second arm section, which are moved relative to one another by the lifting device, the radiation source being arranged on the first arm section and the radiation detector being arranged on the second arm section, and wherein the C-arm is pivotably mounted by one of the first and second arm sections, while the other arm section of the first and second arm sections is the only arm section guided on or in the mounted arm section.

14. The X-ray apparatus as claimed in claim 13, wherein the lifting device is arranged adjacent to a pivot bearing of the C-arm.

15. The X-ray apparatus as claimed in claim 13, further comprising guide rails that are operable to guide the first and second arm sections.

* * * * *

UNITED STATES PATENT AND TRADEMARK OFFICE
CERTIFICATE OF CORRECTION

PATENT NO. : 7,905,658 B2
APPLICATION NO. : 12/348479
DATED : March 15, 2011
INVENTOR(S) : Stefan Gross and Dieter Heinl Page 1 of 1

It is certified that error appears in the above-identified patent and that said Letters Patent is hereby corrected as shown below:

In the claims:
Column 6, claim 5, line 35, "can be" please delete.
Column 6, claim 7, line 43, "can" please delete.

Signed and Sealed this
Nineteenth Day of July, 2016

Michelle K. Lee
*Director of the United States Patent and Trademark Office*